United States Patent [19]
Ivanov et al.

[11] Patent Number: 5,380,497
[45] Date of Patent: Jan. 10, 1995

[54] OXIDATION PROCESS AND APPARATUS

[75] Inventors: Alexy A. Ivanov; Vitaly D. Mescheryakov; Sergey P. Stepanov; Sergey P. Chaykovsky; Alexandr A. Yabrov; Victor P. Gaevoy; Svetlana A. Pokrovskaya; Ecaterina M. Sadovskaya; Valentin S. Sheplev; Youry P. Ermakov, all of Novosibirsk, U.S.S.R.

[73] Assignee: Institute of Catalysis, Novosibirsk, U.S.S.R.

[21] Appl. No.: 33,338

[22] Filed: Mar. 18, 1993

Related U.S. Application Data

[62] Division of Ser. No. 716,635, Jun. 17, 1991, Pat. No. 5,225,575.

[51] Int. Cl.6 .......................... B01J 8/28; F27B 15/08
[52] U.S. Cl. .................................. 422/142; 422/146; 422/145; 422/144; 165/104.16
[58] Field of Search ............... 422/141, 142, 145, 146, 422/144; 165/104.16; 55/208, 267; 96/218

[56] References Cited

U.S. PATENT DOCUMENTS

| | | | |
|---|---|---|---|
| 2,697,653 | 12/1954 | Nicholson | 165/104.16 X |
| 2,989,544 | 6/1961 | Saunders et al. | 422/146 X |
| 2,995,426 | 8/1961 | Keith | 165/104.16 X |
| 3,080,382 | 3/1963 | Rousseau | 422/146 X |
| 3,242,195 | 3/1966 | Way | 549/249 |
| 3,480,408 | 11/1969 | Lacroix | 422/140 |
| 4,971,766 | 11/1990 | Chen et al. | 422/144 |
| 5,143,874 | 9/1992 | Ross | 422/144 X |

FOREIGN PATENT DOCUMENTS 754665 8/1956 United Kingdom .
1272669 7/1986 U.S.S.R. .

*Primary Examiner*—Robert J. Warden
*Assistant Examiner*—E. Leigh Dawson
*Attorney, Agent, or Firm*—William C. Long

[57] ABSTRACT

The present invention relates to the oxidation of organic compounds in a non-uniform fluidized solid catalyst reaction system characterized in that a temperature profile is maintained in the reaction system such that a predominance of the oxidation occurs in a higher temperature zone, unreacted organic compound is adsorbed on the catalyst surface in a lower temperature zone, direct back-circulation of catalyst is restricted between zones and catalyst containing adsorbed organic compound is circulated from the lower temperature zone to the higher temperature zone.

2 Claims, 3 Drawing Sheets

OXIDATION PROCESS AND APPARATUS

This is a divisional of Ser. No. 07/716,635 filed on Jun. 17, 1991. Now U.S. Pat. No. 5,225,575.

BACKGROUND OF THE INVENTION

1. Field of the Invention

The present invention relates to the oxidation of organic compounds using a fluidized, solid catalyst, wherein the oxidation reaction is carried out under controlled non-uniform or non-homogeneous conditions whereby substantially improved product yields are obtained.

2. Description of the Prior Art

The oxidation of organic compounds, for example, the oxidation of ortho-xylene to phthalic anhydride, has been the subject of intensive efforts by many workers throughout the world. Prior work has involved the use of fixed bed catalytic reactions as well as fluid bed reactions.

In fluid bed technology as practiced in the prior art, catalyst is well mixed such that its temperature and the composition of species adsorbed or chemisorbed on its surface are essentially uniform throughout the reaction zone. Prior art patents describing fluid bed operation include the following: U.S. Pat. Nos. 3,565,919, 3,810,921, 3,852,308, 3,862,960, 4,261,899, 3,784,561, 4,705,770, 2,471,853, 2,698,330, 2,863,879, 3,038,911, 3,167,567. 3,210,378, 3,226,338, 3,407,215, 3,455,962 and the like.

SUMMARY OF THE INVENTION

In accordance with the present invention, organic compounds are oxidized by contact with an oxidizing gas in the presence of a fluidized solid catalyst. Specifically, the fluidized solid catalyzed oxidation is carried out under conditions such that the system is in a non-uniform state. In particular, the profile of catalyst temperature and concentration of species on the catalyst surface is controlled in such a way as to enhance the yield over that which can be obtained either by a fixed bed or a conventional fluid bed reactor using the same catalyst composition in each case. Most conveniently, this is accomplished by providing in the fluidized solid reactor at least two distinct zones maintained at different temperatures with provision for restricted catalyst circulation between the zones and with provision for circulating the fluidized solid catalyst containing adsorbed reaction materials from the lower temperature zone to the higher temperature zone. Novel reactor apparatus and packing is provided.

DESCRIPTION OF THE DRAWINGS

The attached

DETAILED DESCRIPTION

Figure 1:
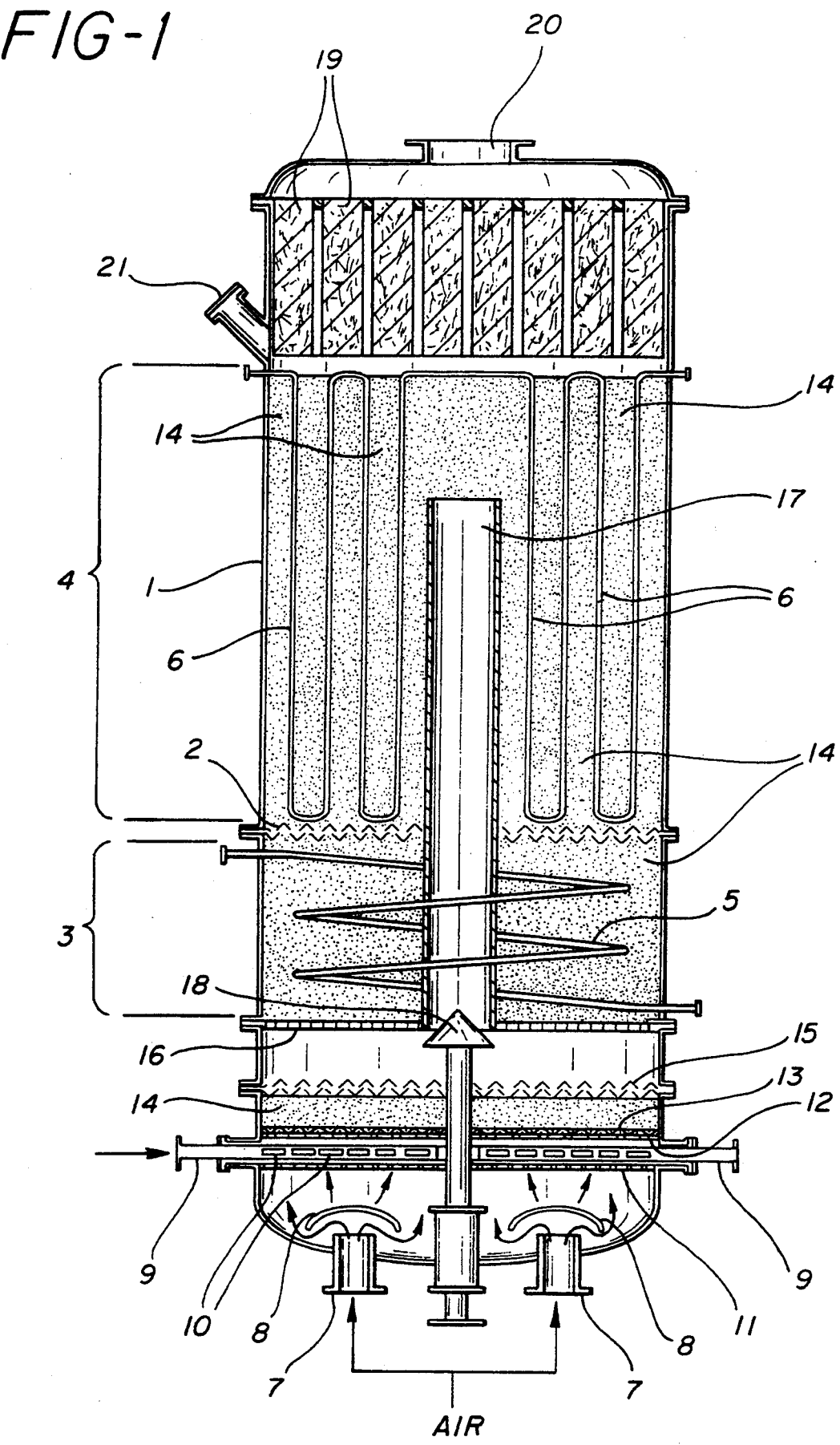
FIG. 1 illustrates in schematic form a reactor useful in carrying out the non-uniform oxidation of the present invention.

In general, fluidized solid catalyzed oxidation reactions have been carried out by prior workers under as nearly well-mixed conditions as is practical. While fluid bed procedures are by nature not truly steady state procedures insofar as catalyst is constantly in motion, is constantly undergoing oxidation state changes and contacts changing gas composition, efforts are made to ensure that a homogeneous or well-mixed state is maintained throughout the reaction zone. Specifically, great care is usually taken by those skilled in the art to ensure that the catalyst temperature and surface state are substantially uniform throughout the entire fluidized solid reaction zone. By virtue of the fluidized solid system, it is possible to intimately contact the reaction gases with the fluidized catalyst and to maintain a great degree of catalyst uniformity throughout the entirety of the oxidation zone.

It has now been discovered, however, that under certain circumstances there is a very significant advantage to operating a fluidized solid oxidation reaction under controlled non-uniform conditions. Specifically, it has been found that by carrying out the oxidation reaction in a plurality of zones maintained at significantly different reaction conditions, with restricted catalyst circulation from the lower temperature to the higher temperature zone, greatly improved product yields can be achieved over those of prior processes.

In accordance with the present invention, a temperature profile is maintained in the fluidized solid reactor by which higher product yields are achieved. A relatively high temperature zone is provided in which oxidation of the organic compound proceeds rapidly and selectively. A relatively low temperature zone is provided in which adsorption or chemisorption of unreacted organic compound on the catalyst surface takes place without excessive, nonselective further oxidation. Finally, catalyst having adsorbed or chemisorbed organic compound is circulated from the lower temperature zone to the higher temperature zone wherein the adsorbed organic compound is oxidized to the desired final product.

In the case of the oxidation of ortho-xylene to phthalic anhydride, the fluidized solid reactor has a first contact zone which is relatively high in temperature and in which the great bulk of the oxidation to phthalic anhydride occurs. Provision is made for the passage of reaction gases and fluidized solid catalyst from this high temperature zone to a subsequent zone of the reactor which is maintained at a temperature which is at least 50° C. lower than the temperature in the first contact zone while restricting direct back-circulation of catalyst from the high temperature zone to the lower temperature zone. In this second, cooler contact zone, species of the reaction materials such as ortho-xylene are adsorbed or chemisorbed on the surface of the fluidized solid catalyst at less reactive conditions. Sufficient residence time is allowed to complete adsorption or chemisorption of the materials on the catalyst surface in this second, cooler reaction zone and catalyst now containing adsorbed or chemisorbed materials is then circulated from the cooler zone back to the high temperature zone wherein the adsorbed materials are further converted to the desired product, e.g. phthalic anhydride.

In especially preferred practice of the invention, packing is provided in certain zones of the fluidized solid reactor, usually in both the higher and lower temperature zones, in order to limit gas bubble size, thus assisting in the effective dispersion and reaction of the reactant gases while in contact with the fluidized solid catalyst. FIG. 3 illustrates an especially preferred packing.

The invention can be illustrated by reference to FIG. 1 which illustrates a suitable reactor for carrying out the invention.

Referring to FIG. 1, reactor 1 represents a fluidized solid oxidation reactor according to the invention. Reactor 1 is divided by baffles 2 into a lower zone 3 and an upper zone 4. Baffles 2 are provided to permit the establishment of two zones of different temperatures within the reactor. In preferred practice, baffles 2 are one-way baffles which permit flow of fluidized solid catalyst and reaction gases essentially only in the upward direction. As depicted in the drawing, baffles 2 are opposed angle irons although other configurations can be used.

Lower zone 3 and upper zone 4 are provided with heat exchange coils 5 and 6 respectively through which reaction heat is removed in order that the temperature in each zone can be separately regulated. Water or molten salt or other commercially available heat transfer fluids can be used as the heat transfer medium.

In the oxidation of ortho-xylene to phthalic anhydride in accordance with the invention, it has been found that the concentration of ortho-xylene in air in the feed to the reactor has a significant effect on reaction selectivity. Higher concentrations of ortho-xylene result in higher selectivities to the desired phthalic anhydride. Generally, ortho-xylene concentrations of about 0.5–5 vol.%, preferably 2–4 vol.% in air give good results.

Because of potential flammability problems at the feed gas concentrations preferably employed, care must be exercised in the introduction of the reactant gases. In the system shown in FIG. 1, the main flow of air enters the reactor via conduits 7 and is distributed by impingement baffles 8. Ortho-xylene in admixture with additional air is introduced into the reactor in such a way as to ensure uniform distribution of the feed across the reactor. One such mode for accomplishing this is illustrated in FIG. 1 wherein ortho-xylene in admixture with additional air is introduced into the reactor through a plurality of radial pipes 9 having slotted openings 10 sized to accomplish the uniform distribution of the feed within the reactor.

Baffle 11 is located below and in close proximity to the ortho-xylene inlet conduits 9. Illustratively, this baffle has low open area, for example, 3% or so. The purpose of the baffle is to localize explosive ortho-xylene concentration mixtures in the least possible volume.

Baffle 12 having a higher open area than baffle 11, illustratively 10% or so, is positioned above and in close proximity to ortho-xylene inlet conduits 9. Screen 13 and packing 14 are positioned above baffle 12. Packing 14 illustratively comprises porcelain pellets 10 mm. in diameter.

One-way baffle 15 is provided through which the feed gases flow into the zone of contact with the catalyst particles which cannot flow downwardly through the baffle. Packing 14 fills essentially the entire space between baffles 12 and 15. Baffle 15 is illustratively opposed angle irons with area open to gas flow of about 20%.

Grate 16 is provided to support packing, preferably of the type shown in FIG. 3 which fills the reactor volume between grate 16 and baffle 2. Similar packing also fills upper zone 4 of the reactor.

In order to provide for division of the reactor into zones of different temperature as is required in accordance with the present invention, there is provided restriction or baffle means 2 for purposes of accomplishing this division. Advantageously, baffle 2 is a one-way baffle such as the opposed angle irons depicted in FIG. 1 through which catalyst and reaction gases pass essentially only in the upward direction. Alternatively, as will be described in connection with FIG. 2 means other than baffle 2 can be provided which restrict direct back-circulation of the catalyst between the zones of different temperature.

A critical feature of the invention is the provision of circulation of catalyst containing adsorbed or chemisorbed reaction materials such as ortho-xylene from cooler zone 4 to higher temperature zone 3. As illustrated in FIG. 1, tube 17 is provided for this circulation of catalyst. Catalyst from lower temperature zone 4 containing adsorbed or chemisorbed unreacted ortho-xylene passes downwardly through tube 17 to the lower zone of the reactor. The rate of catalyst return is regulated by power driven damper 18 by which the open area at the bottom of tube 17 and hence catalyst flow can be regulated.

Catalyst returning via tube 17 from upper zone 4 is admixed with feed ortho-xylene, air and catalyst diffusing downwardly through grate 16 in the zone above one-way baffle 15 and below grate 16 and the resulting fluidized mixture passes upwardly through the reactor high temperature zone 3 and lower temperature zone 4.

Filters 19 are provided to filter catalyst dust from the reaction gas mixture which exits the reactor via conduit 20 to recovery which is not shown. Ports 21 are provided for loading and unloading catalyst.

Obvious modifications to the above can be made and are included within the scope of the invention. The catalyst return line can, if desired, be located external to the reactor. Other one-way baffle configurations permitting gas and solid catalyst flow only in the upward direction can be used. Packing other than that shown in FIG. 3 can be used. It is generally desirable that the packing be very open in configuration with a predominance of the openings sized at least 10 and preferably 20 or more times the catalyst diameter.

Figure 2:
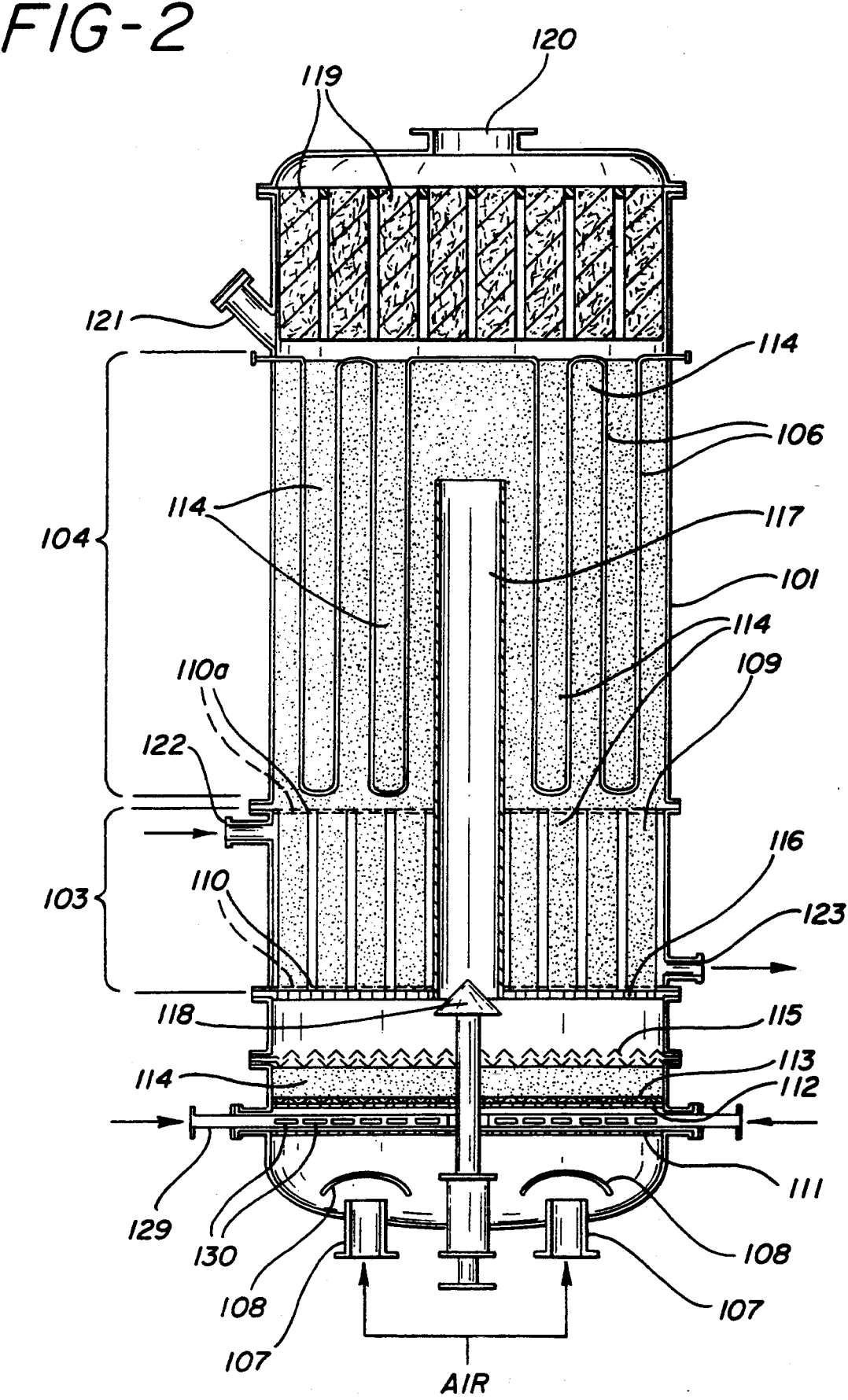
FIG. 2 illustrates in schematic form another reactor configuration useful in carrying out the invention.

Referring to FIG. 2, there is shown schematically an alternative fluidized bed catalytic reactor which, in accordance with the invention, can be operated with very short residence time of the reactant gases and the circulating catalyst in the higher temperature zone while achieving high ortho-xylene conversion in this zone.

Reactor 101 shown in FIG. 2 is similar to Reactor 1 shown in FIG. 1 except in the design of the higher temperature reaction zone 103. In reactor 101, a tube bundle comprised of tubes 109 is provided in the lower section of the reactor. Tube sheets 110 and 110a are provided to which the ends of tubes 109 are securely fastened. Tubes 109 are filled with packing of the type shown in FIG. 3 and catalyst and reactant gases are introduced in a fashion similar to that described in connection with FIG. 1 and pass upwardly through tubes 109. Heat transfer fluid, preferably molten salt, is introduced via line 122 and circulated on the outside of tubes 109 before exiting via line 123.

Generally, the open area of tubes 109 through which catalyst and reactants flow ranges from about 20–80% of the reactor cross sectional area, preferably about 40–60%. Through this reduction in the cross sectional area available for gas flow, the upward velocity in higher temperature zone 103 is increased relative to that in the lower temperature zone 104, thus substantially preventing direct internal back circulation of catalyst and providing the restriction means necessary for practice of the invention.

In operation, the higher temperature zone 103 is preheated, e.g. to 300° C. during reaction start-up by circulation of heated molten salt around the tubes 109. After initiation of the reaction, the exothermal heat of reaction is removed by external cooling (not shown) of the circulating salt. Ortho-xylene conversion is conveniently controlled by regulating the inlet molten salt temperature and/or the rate of circulation.

In the system shown in FIG. 2, the main flow of air enters reactor 101 via conduits 107 and is distributed by impingement baffles 108. Ortho-xylene in admixture with additional air is introduced into the reactor in such a way as to ensure uniform distribution of the feed across the reactor as was described in connection with reactor 1 in FIG. 1. This is illustrated in FIG. 2 wherein ortho-xylene in admixture with additional air is introduced into reactor 101 through a plurality of radial pipes 129 having slotted openings 130 sized to accomplish the uniform distribution of the feed within the reactor.

Baffle 111 is located below and in close proximity to the ortho-xylene inlet conduits 129. Illustratively, this baffle has low open area, for example, 3% or so. The purpose of the baffle is to localize explosive ortho-xylene concentration mixtures in the least possible volume.

Baffle 112 having a higher open area, illustratively 10% or so, is positioned above and in close proximity to ortho-xylene inlet conduits 129. Screen 113 and packing 114 are positioned above baffle 112. Packing 114 illustratively comprises porcelain pellets 10 mm. in diameter.

One-way baffle 115 is provided through which the feed gases flow into the zone of contact with the catalyst particles which cannot flow downwardly through the baffle. Packing 114 fills essentially the entire space between baffles 112 and 115. Baffle 115 is illustratively opposed angle irons with area open to gas flow of about 20%. Grate 116 is provided at lower ends of tubes 109 to support packing contained therein.

A critical feature of the invention is the circulation of catalyst containing adsorbed or chemisorbed reaction materials such as ortho-xylene from cooler zone 104 to higher temperature zone 103. As illustrated, tube 117 is provided for this circulation of catalyst. Catalyst from lower temperature zone 104 containing adsorbed unreacted ortho-xylene passes downwardly through tube 117 to the lower zone of the reactor. The rate of catalyst return is regulated by power driven damper 118 by which the open area at the bottom of tube 117 and hence catalyst flow can be regulated.

Catalyst returning via tube 117 from upper lower-temperature zone 104 is admixed with feed ortho-xylene and air in the zone above one-way baffle 115 and below tube sheet 110 and the resulting fluidized mixture passes upwardly through the higher temperature zone 103 via reactor tubes 109 and thence through the lower temperature zone 104.

Filters 119 are provided to filter catalyst from the outlet reaction gas mixture which exits the reactor via conduit 120 to recovery which is not shown. Ports 121 are provided for loading and unloading catalyst.

In accordance with the invention, a predominance but not all of the feed ortho-xylene conversion to phthalic anhydride takes place during the initial passage of the reaction mixture through the higher temperature zone—zone 3 in the case of FIG. 1 and zone 103 in the case of FIG. 2. Specifically, in order to achieve the advantages of the invention, the reaction mixture comprised of reaction gases and fluidized solid passing upwardly through one-way baffle 2 from zone 3 to zone 4 in FIG. 1 or through tubes 109 from zone 103 to zone 104 of FIG. 2 contains substantial amounts of unreacted ortho-xylene. In most advantageous operation, about 10 to 30% of the ortho-xylene fed to the reactor is unreacted during the initial pass through the higher temperature zone and is contained in the gases passing to the lower temperature zone.

The reaction temperature in the higher temperature zone is illustratively 300°–500° C. and is at least 50° C. higher than the temperature in the lower temperature zone. At the conditions of temperature and with the presence of unreacted ortho-xylene maintained throughout the higher temperature zone, high selectivity in the oxidative formation of phthalic anhydride therein is achieved.

In the cooler zone, zone 4 in FIG. 1 and zone 104 in FIG. 2, with temperatures illustratively maintained at 200°–350° C., unreacted ortho-xylene is strongly adsorbed or chemisorbed on the surface of the catalyst while there is little or no further oxidation. Product phthalic anhydride is not significantly adsorbed or chemisorbed on the catalyst and passes with the exit gases to recovery while solid catalyst particles and adsorbed or chemisorbed ortho-xylene return to the higher temperature zone. In the higher temperature zone, at the higher temperature maintained therein the adsorbed or chemisorbed ortho-xylene returning with the catalyst is rapidly and selectively converted to phthalic anhydride along with ortho-xylene entering with the gas feed.

It is generally advantageous that the higher temperature zone be considerably smaller in volume than the lower temperature zone. Best results are achieved where the lower temperature zone is 2–10 times greater in volume than the higher temperature zone.

In addition to the above considerations, it has further been found that best results are achieved where the a conversion of ortho-xylene in the high temperature zone is 60–95%, preferably 70–90%.

Generally speaking, the superficial vapor velocity in the lower temperature zone is suitably 3–5 times the minimum fluidization velocity for best heat exchange. In the higher temperature zone, the superficial vapor velocity should not exceed about 90% of the entrainment velocity of the catalyst employed.

While the invention has been described in terms of two different temperature zones in a single reactor, as an alternative, two separate reactors maintained at different temperatures may be provided with catalyst circulation means from the lower temperature reactor to the higher temperature reactor. Also, it is possible to carry out the invention using a reactor comprised of more than 2 zones of different temperature. It is critical, however, in practice of the invention that the bulk but not all of the conversion of ortho-xylene newly fed to the reactor be carried out at the higher reaction temperature with unreacted ortho-xylene passing to the cooler zone where it is adsorbed on the catalyst surface at the lower temperature and then returned to the higher temperature zone to complete the conversion to phthalic anhydride.

In a particular practice, ortho-xylene is oxidized to produce phthalic anhydride. According to the invention, other starting materials can be oxidized to produce a broad range of products. However, in its most preferred aspect, the unsteady state or non-equilibrium fluid bed oxidation of the present invention is applied to the oxidation of ortho-xylene to produce phthalic anhydride.

Catalysts which are employed in accordance with the present invention are of a generally known type as illustrated in the many fluid bed or fixed bed phthalic anhydride production patents referred to earlier in the instant specification. Generally speaking, the catalysts are of a vanadium oxide on titanium oxide combination and are prepared by procedures which are known to those skilled in the art.

The oxidizing gas which is employed in the invention is a molecular oxygen containing gas, most preferably air.

Concentrations of oxygen which are higher or lower than that found in air can be employed. Inert diluents can be used with the molecular oxygen, suitable diluents being carbon dioxide, nitrogen, helium, argon and the like. By far, however, the most preferred oxidizing gas is air.

It has been found that through practice of the present invention, i.e. conducting the oxidation at controlled non-uniform conditions in the fluidized solid reaction system, substantially improved yields of the desired end product are achieved as compared to conventional fixed bed procedures as well as conventional fluid bed procedures where homogeneous conditions are maintained as best possible throughout the fluidized solid reaction zone. Specifically, in the oxidation of ortho-xylene to produce phthalic anhydride, substantially improved yields of phthalic anhydride are achieved as a result of the unsteady state fluid bed oxidation system of the present invention.

Figure 3A:
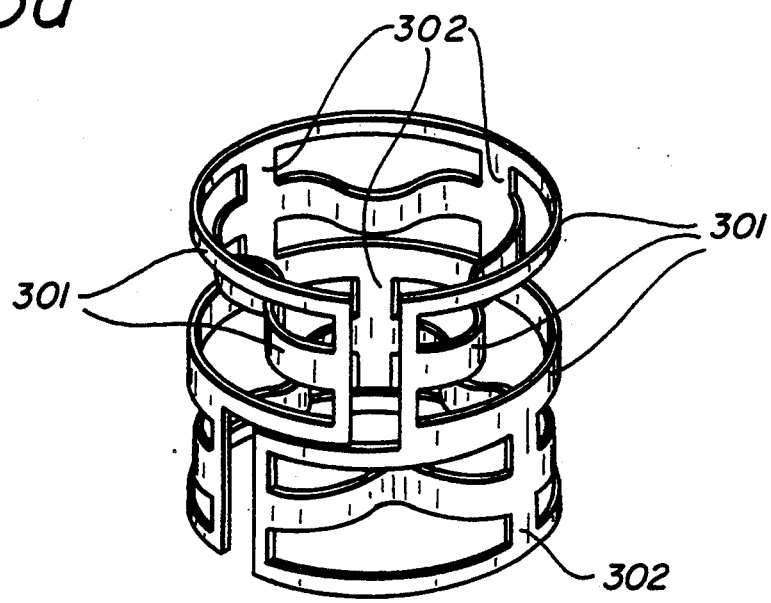
FIG. 3 illustrates reactor packing which is particularly useful in carrying out the invention.
Figure 3B:
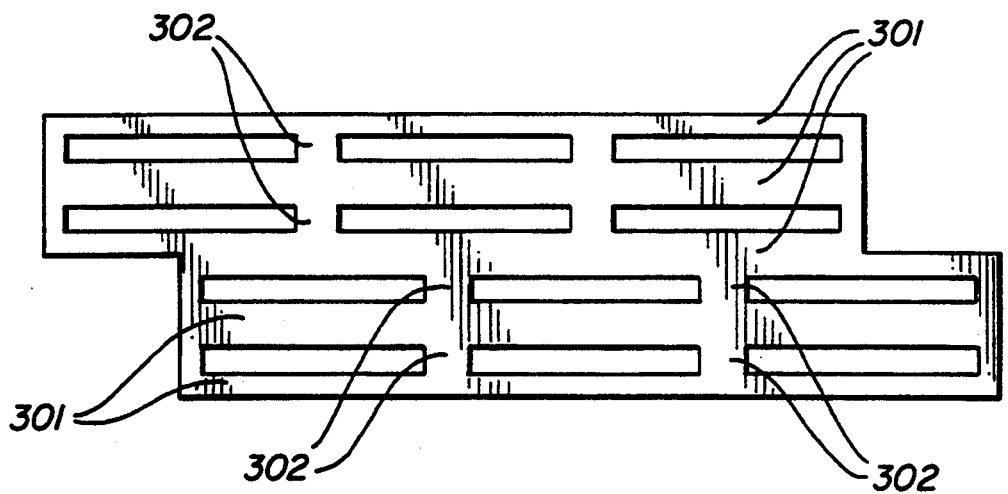

In carrying out the oxidations of the present invention, the use of packing of the type shown in FIG. 3 is especially advantageous. FIG. 3a illustrates a finished packing shape suitable for use while FIG. 3b illustrates a suitable configuration prepared from metal sheet before being formed into the final shape.

The packing is preferably made of stainless steel, although other materials can be used. Advantageously, a sheet of stainless steel is stamped by conventional procedures to produce the configuration shown in FIG. 3b. Thereafter, the flat article is shaped as by rolling or bending into the final packing configuration shown in FIG. 3a. For ease of understanding the same numbering is shown in FIG. 3b before shaping and in FIG. 3a which is after rolling or bending.

The size of the packing can vary considerably depending, for example, on the size and configuration of the reactor in which it will be used. A cylindrical shape of equal diameter and height is suitable, although the shape can vary. Preferred is the provision of a cylindrical shape as shown in FIG. 3a with narrow metal strip members 301 arranged perpendicular to the cylinder axis, some of which are circular around the cylinder axis and some of which are bent inwardly toward the cylinder axis. The strips are interconnected by narrow connecting strips 302 disposed parallel to the cylinder axis. Preferably, the said perpendicular strips 301 are alternately circular and bent toward the axis. The packing is configured to permit ready passage therethrough of reacting gases and catalyst; generally, most openings in the packing units should be at least 10 and preferably 20 or more times the diameter of the catalyst particles.

Most desirably, the narrow strip members perpendicular to the cylinder axis and bent inwardly are uniformly offset from each other to provide best gas dispersion.

Example 1

Three $m^3$ catalyst (weight ratio of components: $SiO_2$(carrier):$V_2O_5$:$TiO_2$:$K_3PO_4$=100:25:4:0.6) were loaded into a reactor as shown in FIG. 1. The reactor had an inner diameter of 1.6 m, a height of the lower reaction zone of 0.9 m and a height of the upper reaction zone of 3.5 m. The heat exchange surfaces of the cooling coils was 1.56 $m^2$ in the high temperature lower zone and 28 $m^2$ in the lower temperature upper zone. Both zones were filled by packing of type shown in FIG. 3a with dimensions of 30 mm×30 mm, made of stainless steel. The catalyst was in the form of spheres having a diameter of 0.2–0.6 mm. A feed mixture of 283 kg. per hour ortho-xylene vapor and 1931 standard $m^3$ per hour of air was fed into the reactor. By adjusting coolant temperatures inside of the coils of the lower and the upper coolers there were established temperatures of 360° C. and 250° C. for the lower and the upper reaction zones, respectively. The catalyst recirculation ratio from the lower temperature zone to the higher temperature zone was 7 liters/sec. The molar yield of phthalic anhydride obtained was 92%.

Example 2

Conditions of the test are the same as in Example 1 except that the height of the higher temperature lower reaction zone is 1.3 m and that of the upper zone, 3.1 m. Yield of phthalic anhydride comprises 77 vol.%. This example when compared with Example 1 illustrates that improved results are achieved at higher volumetric ratios of the lower temperature zone to the higher temperature zone.

Comparative Example A

The conditions of the test are the same as in Example 1 except the temperatures of the lower and the upper reaction zones are maintained the same, i.e. 330° C. Conversion of ortho-xylene is 99.7%, yield of phthalic anhydride comprises 67 vol.%. A comparison of these results with those shown above illustrates the improvement achieved through practice of the invention.

Example 4

Ortho-xylene vapor is fed at the rate of 84.7 g. per hour in admixture with 2 standard $m^3$ per hour of air into the bottom of a pilot reactor, which consists of two electric jacketed sections flanged together: the lower section has an inner diameter of 70 mm and a height of 0.8 m; the upper section has an inner diameter of 100 mm and a height of 2.5 m. A cooling coil is installed in each section. An external catalyst recirculation line is located at the level of 1.5 m above the flange joint and connects the upper section with the lower at a point 0.75 below the flange joint. The packing is the same as in Example 1. The catalyst is the same as Example 1 and is charged in amount of 8 liters. The temperature in the lower reaction zone is maintained in the range 320°–380° C. while that in the upper is maintained at 250° C. By provision of the two sections of different inner diameter, the gas velocity in the lower zone is considerably higher than that in the upper zone, thus restricting direct back-circulation of catalyst between zones. The molar yield of phthalic anhydride is 95%.

What is claimed:

1. A reaction vessel comprising a first reaction zone adapted for the contact of oxygen and hydrocarbon reactant gases and fluidized solid catalyst particles, restriction means located above said first reaction zone adapted to permit passage of both reactant gases and catalyst particles from said first zone to a second reaction zone located above the restriction means while at least lessening back-circulation of solid particles from the second reaction zone to the first reaction zone, a second zone located above the restriction means adapted for the contact of oxygen and hydrocarbon reactant gases and fluidized solid catalyst particles, said second reaction zone being 2-10 times greater in volume than said first reaction zone, a zone of contact for mixing oxygen and hydrocarbon reactant gases and catalyst particles located below the first reaction zone, means for introducing oxygen and hydrocarbon reactant gases and catalyst from said zone of contact into said first reaction zone, means for recovering product gases from said second reaction zone, means for regulating the temperature in each of said zones and for maintaining temperature of said first zone higher than that of said second zone, and axially located conduit means for returning solid catalyst particles from the second reaction zone to said zone of contact.

2. The reaction vessel of claim 1 wherein said restriction means is a one-way baffle.

* * * * *